United States Patent [19]
Le Grazie

[11] Patent Number: 5,538,734
[45] Date of Patent: Jul. 23, 1996

[54] 5-METHYLTETRAHYDROFOLIC ACID, 5-FORMYL-TETRAHYDROFOLIC ACID AND THEIR PHARMACEUTICALLY ACCEPTABLE SALTS FOR USE IN THE THERAPY OF DEPRESSIVE DISTURBANCES

[75] Inventor: Christina Le Grazie, Milan, Italy

[73] Assignee: Bioresearch S.p.A., Milan, Italy

[21] Appl. No.: 386,188

[22] Filed: Feb. 9, 1995

Related U.S. Application Data

[63] Continuation of Ser. No. 995,958, Dec. 23, 1992, abandoned, which is a continuation of Ser. No. 471,526, Jan. 29, 1990, abandoned.

[30] Foreign Application Priority Data

Jan. 31, 1989 [IT] Italy ................................. 19261A89

[51] Int. Cl.$^6$ ............................. A61K 9/02; A61K 9/28; A61K 31/505
[52] U.S. Cl. ......................... 424/436; 424/449; 424/468; 424/474; 424/480; 424/490; 424/494; 514/269; 544/255; 544/261
[58] Field of Search ...................... 424/436, 449, 424/468, 474, 480, 494, 490; 544/255, 261; 514/269

[56] References Cited

U.S. PATENT DOCUMENTS

| | | | |
|---|---|---|---|
| 4,834,985 | 5/1989 | Elger et al. | 424/468 |
| 4,959,472 | 9/1990 | Wood et al. | 544/258 |
| 5,059,595 | 10/1991 | Le Grazie | 424/468 |

FOREIGN PATENT DOCUMENTS

| | | |
|---|---|---|
| 0164964 | 12/1985 | European Pat. Off. . |
| 0290819 | 11/1988 | European Pat. Off. . |
| 1572137 | 7/1980 | United Kingdom . |
| 2072504 | 10/1981 | United Kingdom . |

OTHER PUBLICATIONS

Botez et al, "Folate Deficiency and Decreased Brain 5 Hydroxy-tryptamine Synthesis in Man and Rat", Nature, vol. 278, Mar. 8th 1979, p. 182.
Manzoor et al, "Folak-Responsive Neuropathy: Report of 10 Cases", British Medical Journal, 15 May 1976, p. 1176.
Reynolds et al, "Effects of Folic Acid On the Mental State and Fit-Frequency of Drug-Treated Epileptic Patients", The Lancet, May 20, 1967.
Drug Information for the Consumer United States Pharma-Copeial Convention, Inc., Eighth Edition, 1988, p. 662.

Primary Examiner—Amy Hulina
Attorney, Agent, or Firm—Birch, Stewart, Kolasch & Birch

[57] ABSTRACT

The present invention refers to the use of 5-methyltetrahydrofolic acid, of 5-formyltetrahydrofolic acid and of their pharmaceutically acceptable salts for the preparation of controlled release pharmaceutical compositions suitable for the use in the therapy of depressive disturbances, in particular major depression, dysthymia or depressive neurosis and not otherwise specified depressive disturbances, independently from folate plasmatic levels, and to the pharmaceutical composition thus prepared.

8 Claims, 13 Drawing Sheets

5-METHYLTETRAHYDROFOLIC ACID, 5-FORMYL-TETRAHYDROFOLIC ACID AND THEIR PHARMACEUTICALLY ACCEPTABLE SALTS FOR USE IN THE THERAPY OF DEPRESSIVE DISTURBANCES

This application is a continuation of application Ser. No. 07/995,958 filed on Dec. 23, 1992, now abandoned, which is a continuation of application Ser. No. 07/471,526 filed on Jan. 29, 1990, now abandoned.

DESCRIPTION

The present invention relates to the use of 5-methyltetrahydrofolic acid, of 5-formyltetrahydrofolic acid and of their pharmaceutically acceptable salts for the preparation of pharmaceutical compositions suitable for the use in the therapy of depressive disturbances, and in particular major depression, dysthymia or depressive neurosis, independently from plasmatic folate levels, and to the thus obtained pharmaceutical compositions.

Depressive disturbances are found very frequently in general medical practice and in particular in psychiatric practice.

For their therapy, antidepressive tricyclic compounds, monoamine oxidase inhibitors, certain antipsycotic drugs, litium carbonate and anticonvulsive therapy were used up to now.

One should not overlook the fact that practically all drugs employed up to now in the therapy of depressive disturbances are potentially lethal and in case of overdosage and may also be responsible for a series of morbid events, even when used under clinical supervision (Goodman & Gilman—The Pharmacological Basis of Therapeutics—6th Ed.). In the therapy of depressive disturbances the most widely used drugs are tricyclic compounds which are all similar in their efficacy but present a long series of side effects on the central nervous system, on the autonomous nervous system and on the cardiovascular system. Some of the side effects which have been described are due to anticholinergic action (xerostomia, blurred vision), where gait may be irregular, and the individual feels clumsy and fatigued. The pharmacological effects are generally disagreable and cause anxiety and disconfort. These drugs have, furthermore, a sedative effect and are occasionally used as hypnotics. In patients treated with tricyclic drugs an increased tendency to arhythmia, insurgency of miocardial infarction, re-acutization of cardiac insufficiency, tachycardia have been observed; frequent cases of sudden death are also reported; even with therapeutic dosage, orthostatic hypotension is frequently observed.

These are only some of the numerous toxic effects caused by tricyclic antidepressants, and the dangers involved in their therapeutic use are evident.

Also known are 5-methyltetrahydrofolic acid and 5-formyltetrahydrofolic acid, which are two co-factors of folic acid, structurally correlated to pteroyl-glutamic acid, a structure which mammal cells are unable to synthesize, and which they utilize in reactions involving transfer of monocarbonic groups.

Such reactions lead mainly to the synthesis of the purine ring and of thymidylate and to neogenesis of methyl groups.

In the present invention, for greater clarity and simplicity, the expression 5-methyltetrahydrofolic acid and the initials MTHF refer to compounds having the following complete chemical denomination (±)-L-5-methyl-5,6,7,8-tetrahydrofolic acid and (−)-L-5-methyl-5,6,7,8-tetrahydrofolic acid and their salts, whereas the expression 5-formyltetrahydrofolic acid and the initials FTHF refer to compounds having the following complete chemical denomination (±)-L-5-formyl-5,6,7,8-tetrahydrofolic acid and (−)-L-5-formyl-5,6,7,8-tetrahydrofolic acid and their salts. In the blood, the folate pool is represented in good part by 5-methyltetrahydrofolic acid and 10-formyltetrahydrofolic acid, which are captured by the cells through a transport system which is specific for reduced folates.

The same system, present in choroid plexa, transports MTHF from blood to the cerebrospinal fluid; this transport is followed by a passive fluid diffusion to cervical cells.

The physiological functions of folates in the central nervous system (CNS) are many and may be linked to the synthesis of sulfo-adenosyl-L-methionine and to the intervention in the metabolism of certain ammino acids: glutamic acid, glycine, serine. Through these actions the folates may modulate the activity of certain aminergic system; folates are furthermore essential for purine synthesis and therefore for the production of ATP and GTP and of nucleic acids.

The importance of folates at the CNS level is well known, and it is experimentally demonstrated by the fact that intracortical and intracisternal administration to the animal of folic co-enzymes leads to the insurgence of epileptiform convulsions (Obbens E. A. M. T. Hommes O. R.: J. Neurol. Sci: 1973; 20: 223–9).

Clinically the folate role in the CNS is confirmed by the fact that a high percentage of hypofolatemic subjects present neuropsychiatric disturbances (Shorvon S.D. et al. Brit. Med. J. 1980, 281: 1036).

In hypofolatemic subjects, the administration of folates allows obtaining an improvement of neuropsychiatric disturbances associated with a deficiency of this vitamin.

(Butez, M. I. et al. Folic Acid in Neurology, Psychiatry and Internal Medicine Eds. Botez M. J. Reynolds, E. H. Raven Press, N.4 1983, p. 435–461).

However, the therapeutic usage of folic acid co-factors was limited up to now to the prevention and treatment of deficiencies of these vitamins, that is, to the treatment of hypofolatemic patients. No adimistrations for therapeutic ends to normofolatemic patients were ever made.

Purpose of the present invention is to obtain an efficient therapy of depressive disturbances, with the aid of pharmaceutical compositions, which are different from the drugs employed up to now and are free of the numerous and dangerous side effects observed in all classes of drugs utilized up to now in the therapy of depressive disturbances.

We have now found that pharmaceutical compositions with controlled release, variable form 15 minutes to 8 hours, preferably from 20 to 60 minutes, containing 5 to 200 mg, preferably 10 to 50 mg, MTHF or FTHF (in the following indicated for short as controlled release MTHF and FTHF) exert unexpected pharmacological activities when used in the therapy of depressive disturbances, in particular of major depression, of dysthymia and of non otherwise specified depressive disturbances, and that such activity is present independently of hematic folate levels.

The Diagnostic and Statistic Manual of Mental Disorders-Third Edition, Revised DSM III R—published by the American Psychiatric Association, Washington, D.C. 1987, codifies and describes as follows the depressive episodes, and in particular the major depressive episode:

296.2x—Major Depressive Episode. Single episode, from mild to severe 296.3x—Major Depressive Episode Recurring, from mild to severe The same manual defines the following diagnostic criteria for the Major Depressive Episode:

A—Disphoric mood or loss of interest or pleasure in all or almost all usual activities or pastimes. The disphoric mood is characterized by attributions such as: depressed, gloomy, helpless, "down", dejected, irritable.

The mood disturbance must be pre-eminent and relatively persistent, but not necessarily the predominant symptom, and does not concern temporary changes from one disphoric mood to another, as for instance from anxiety to depression, to anger, as the ones observed in severe psychotic disturbances.

B—At least four of the following symptoms have been present almost every day for a period of at least two weeks:

1—scarce appetite and significant weight loss

2—insomnia or hyperynsomnia

3—psychomotor agitation or retardation (not only subjective feelings of restlessness or being slowed down);

4—loss of interest or pleasure in the ordinary activities or decrease in sexual impulse, not limited to a period during which the subject presents delusion or hallucinations;

5—loss of energy, fatigue;

6—feelings of worthlessness, personal inadequacy, excessive or inappropriate guilt (all these symptons may be delirious;)

7—Complaints or signs of a diminished ability to think or concentrate; for example slowing down of thoughts or indecision unassociated with a marked slow down in associative connections or with incoherence;

8—recurrent thoughts of death, suicidal ideation, wish of being dead or suicidal attempts;

9—none of the following elements dominates the clinical pattern when the effective syndrome (that is the symptoms of the above A and B criteria) is absent, that is prior to the exordium and after the remission;

1. Anxiety connected with mood-incongruent delusions or hallucinations;

2—Strange behaviour

D—Not superimposed on schizophrenia schizophreniform disorder or psychotic disorder E—Not due to any organic mental disturbance or bereavement Uncomplicated The dysthimia disturbances are codified by DSM III R as 300.40 and the relative diagniostic criteria are reported as follows;

A. During the last two years the individual was disturbed, for most or all the time, by symptoms characteristic of a depressive syndrome, however of insufficient seriousness and duration to satisfy the criteria of a Major Depressive Episode.

B. The depressive syndrome phenomena may be relatively persistent or interrupted by periods of normal mood which last from a few days to a few weeks, but not more than a few months.

C. During the depressive periods the mood is prevailingly depressed (gloomy, dejected) or there is a marked loss of interest or pleasure in all or almost all usual activities and pastimes.

D. During the depressive periods at least three of the following symptoms are present;

1. Insomnia of hyperynsomnia;

2. Low energy level or persistent fatigue;

3. Feelings of inadequacy and worthlessness, self reproach;

4. Diminished efficiency and productivity at school, at work and in the home;

5. Diminished attention, concentration or ability to think clearly;

6. Social retirement;

7. Loss of interest and enjoyment in pleasurable activities;

8. Irritability and excessive anger;

9. Inability to respond with manifest pleasure to praise and recognition;

10. Less active and talkative than usual, feels slowed down and restless;

11. Pessimistic feelings about the future, complaints regarding passed events or selfpity;

12. Crying spells;

13. Recurrent thoughts of death or suicide.

E—Absence of psychotic features, such as delusion, hallucinations, or loosening of associations.

F—If the disturbance is superimproved on a pre-existent mental disturbance, such as Compulsive Obsessive Disturbance, Alcohol Dependency, the depressed mood, can be clearly distinguished from the usual individual mood for its intensity and its effects on functioning. Depressive disorders not otherwise specified are codified by DSM III R os 311.00 and the diagnostic criteria are reported as follows: depressive episodes, generally of moderate intensity, but occasionally accentuated, which do not have the specific characters of maniac-depressive psychosis or of other forms of psychotic depression and which do not appear to be associated with stressful situations or with other characteristics specified for neurotic depression.

EXAMPLES

1—Major Depressive Episode superimposed on residual schizophrenia.

2—Mild recurrent depressive episode which does not satisfy the diagnostic criteria of dysthymia.

3—Depressive episodes not stress-induced which do not satisfy the diagnostic criteria of Major Depression, single episode.

The characteristics and advantages of the present invention will be mope clearly evidenced by the summary description of some significant clinical studies selected among the many made employing the compositions according to the present invention.

For a preliminary evaluation of the ability of the substances under examination to produce improvement in the neuropsychiatric parameters, we have employed the Wittenborn scale (Wittenborn J. R.; Holzberg J. D., Simon B., Psychiatric Diagnoses Genet. Psycol. Monogr. 1953, 47: 237) reported in Table I.

The Wittenborn scale comprises 9 groups of symptoms, each of which identifies a specific diagnosis: to each group a specific score is associated, variable from 0 (absence of symptoms) to 10 (highest severity of symptoms).

TABLE I

Psychiatric rating scale by WITTENBORN JR., HOLZBERG J D., and SIMON B. ("Psychiatric Diagnoses", Genet. Psychol. Monogr. 47: 237, 1953).

| GROUPS OF SYMPTOMS | DIAGNOSIS |
| --- | --- |
| I | Acute anxiety |
| II | Hysterical Neurosis, Conversion type |
| III | Maniac state |
| IV | Depressed state |
| V | Schizophrenic Excitement |
| VI | Paranoid condition |
| VII | Schizophrenia Paranoid type |
| VIII | Schizophrenia Disorganized type |
| IX | Phobic Compulsive |

A modification of the parameter score of the Wittenborn scale, following an administration of drugs, gives significant indications about the influence of the drug on the CNS and allows to identify the group of symptoms on which the therapeutic action is more manifest. By the use of such scale we have ascertained that the normal therapeutic dosage of folates in non controlled release form administered to normofolatemic subjects, that is, to subjects presenting normal folate plasmatic levels (comprised between 3 and 17 ng/ml), does not exert any pharmacological important activity at the CNS level. In fact, the treatment of non-hypofolatemic subjects (plasmatic folates comprised between 3 and 17 ng/ml) suffering from major depression or from dysthymia or from not otherwise specified depressive disorders, with 50 mg/day of MTHF or FTHF in non controlled release form does not exert any significant effect on the neuropsychiatric parameters evaluated by means of the Wittenborn scale.

Figure 1A:
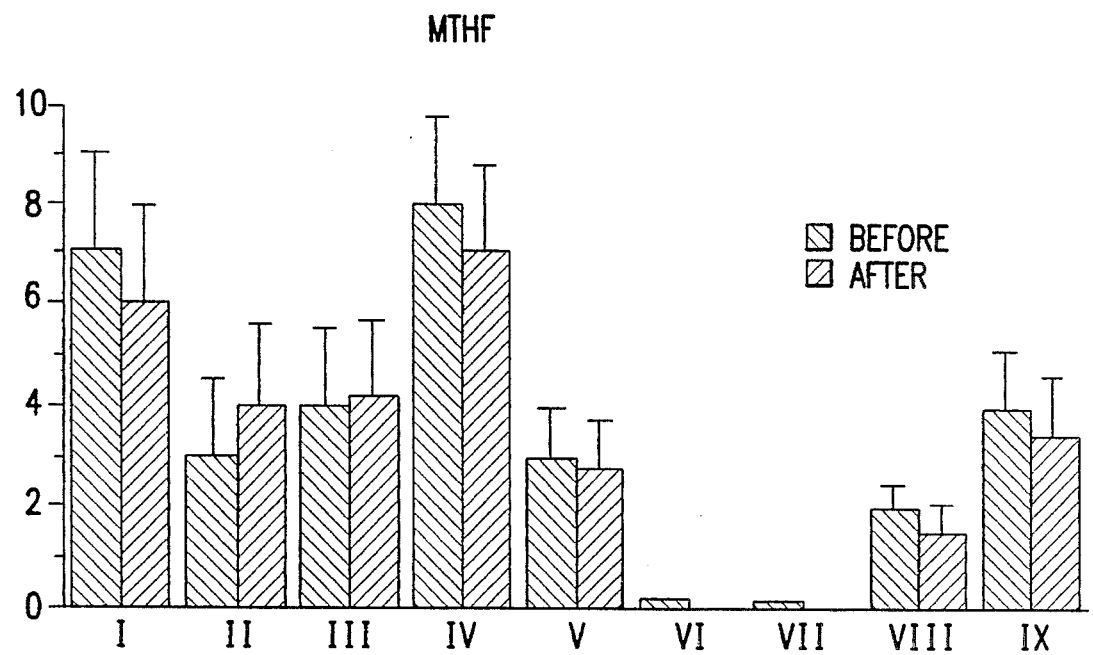
FIGS. 1A and 1B show the effect of MTHF and FTHF in non-controlled release form on the neuropsychiatric parameters evaluated by means fo the Wittenborn scale of normofolatemic subjects.
Figure 1B:
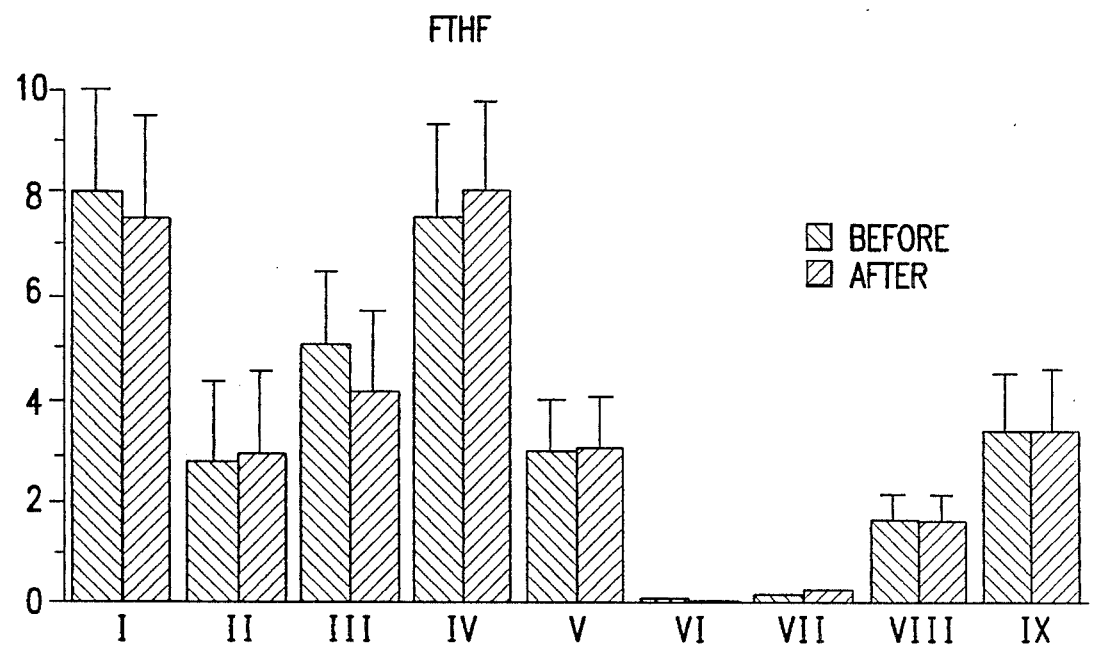
Figure 2A:
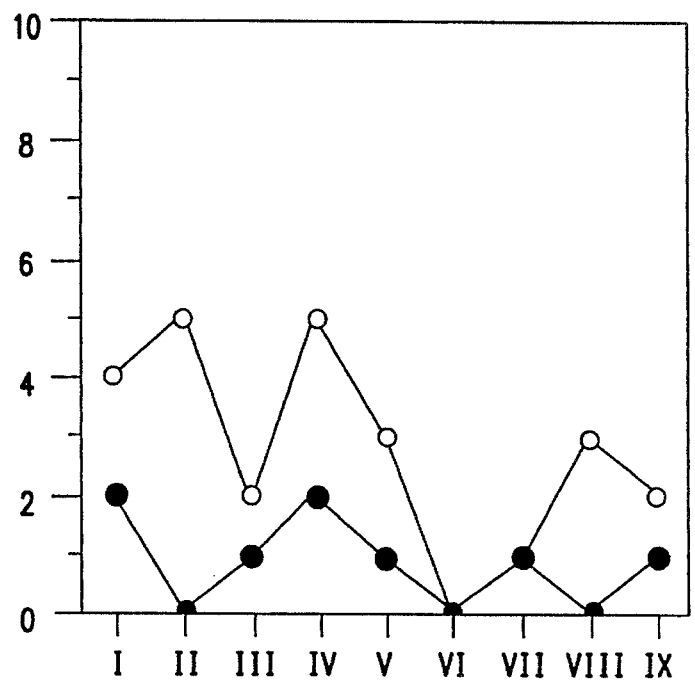
FIGS. 2A–2E shows the results of the treatment of five normofolatemic patients with controlled release MTHF.
Figure 2B:
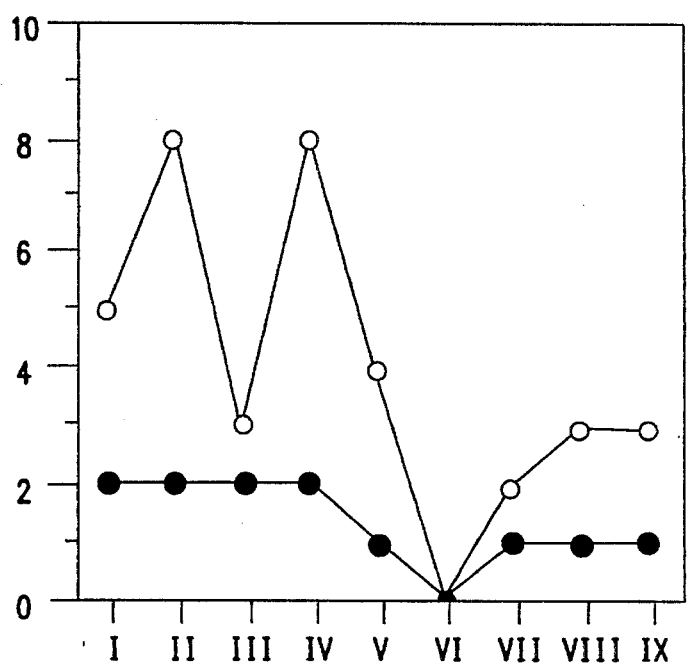
Figure 2C:
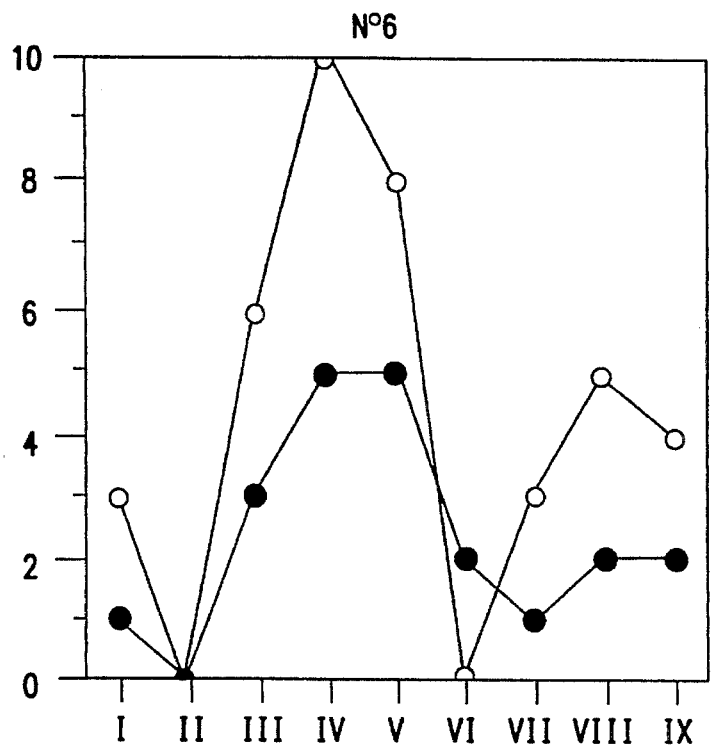
Figure 2D:
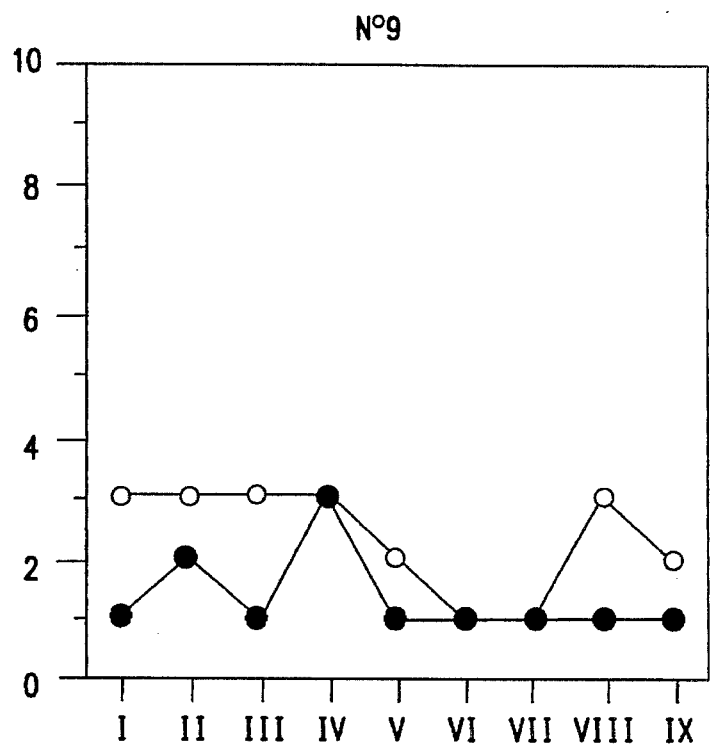
Figure 2E:
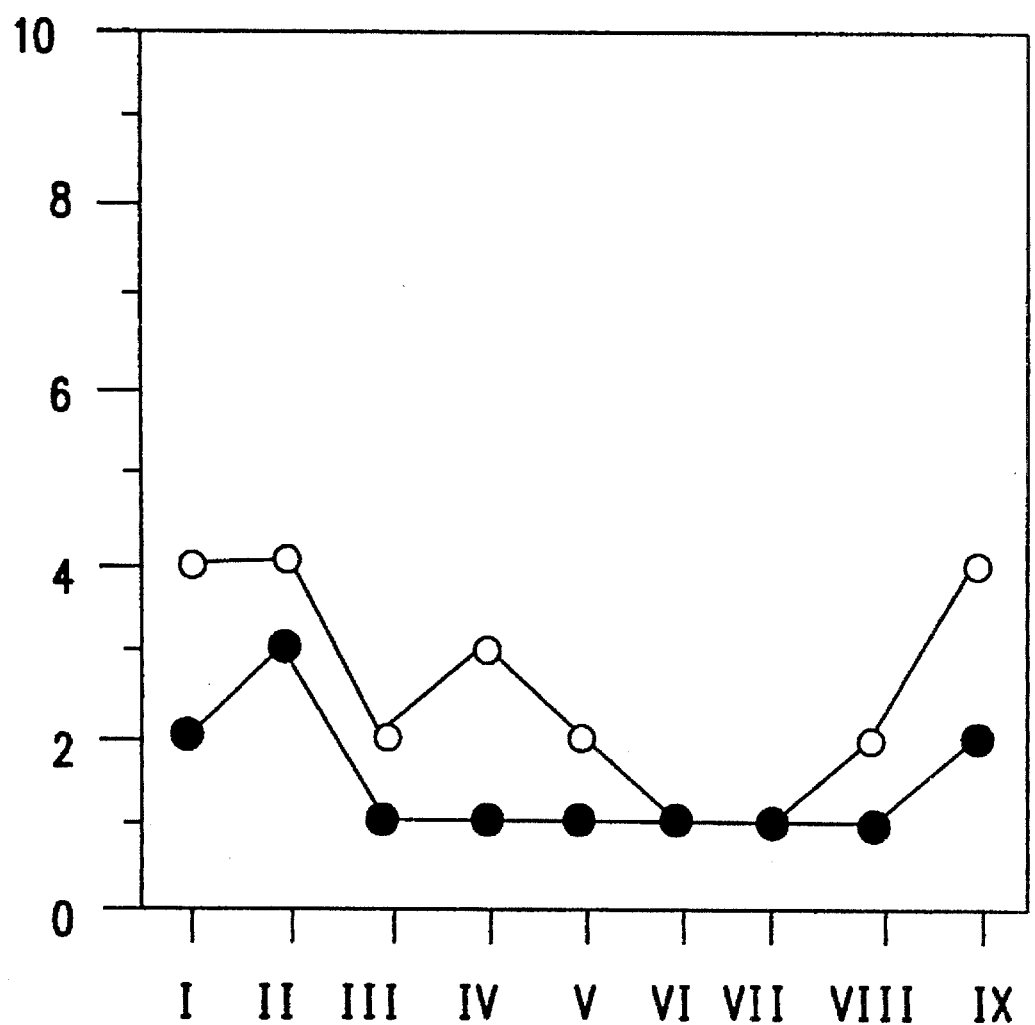
Figure 3A:
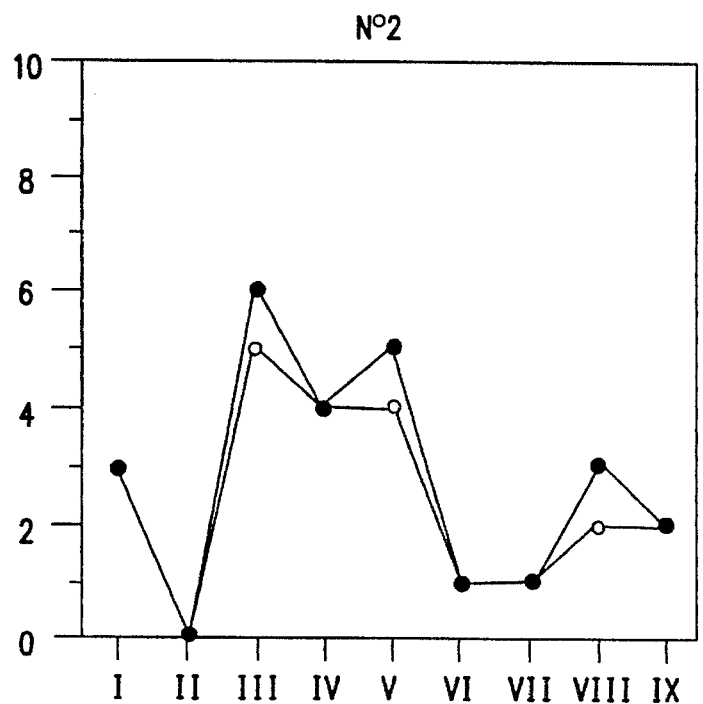
FIGS. 3A–3E show the results of the treatment of five normofolatemic patients with placebo.
Figure 3B:
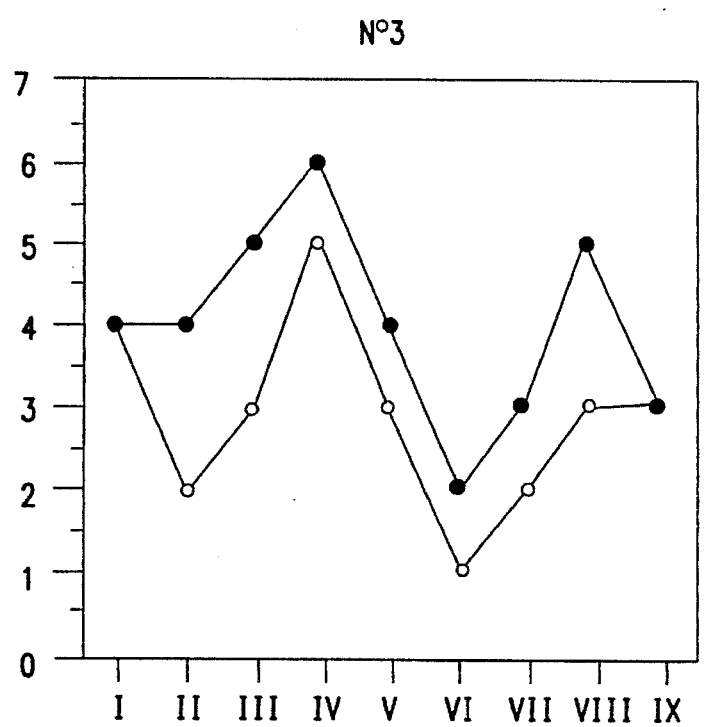
Figure 3C:
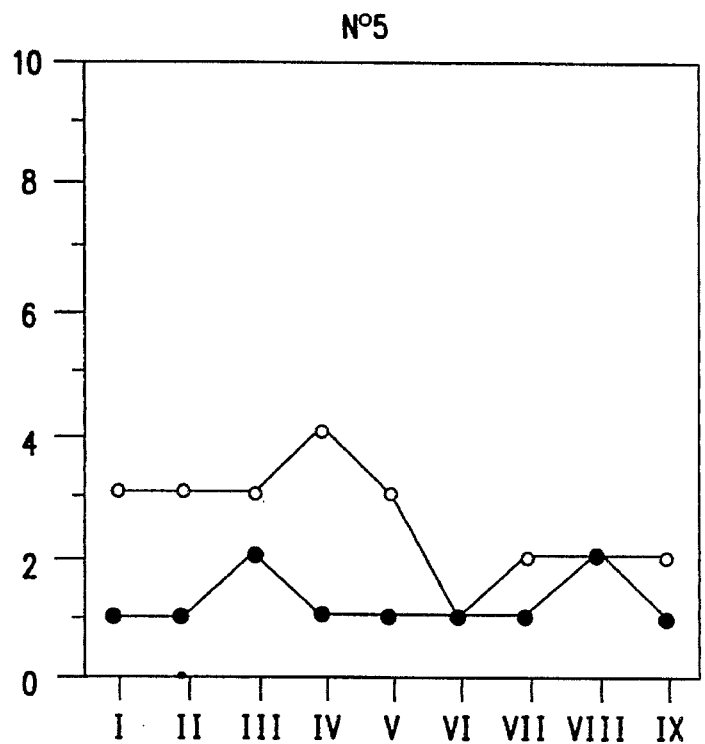
Figure 3D:
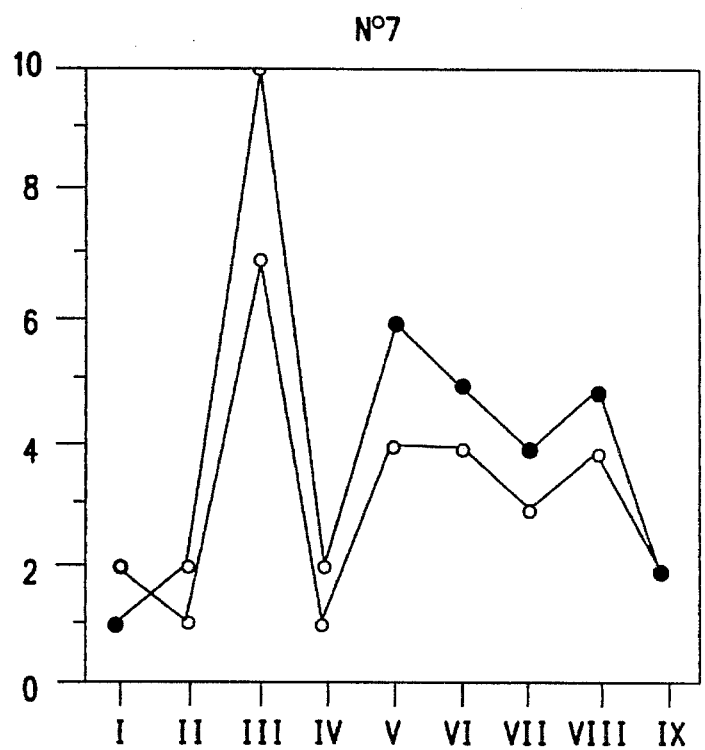
Figure 3E:
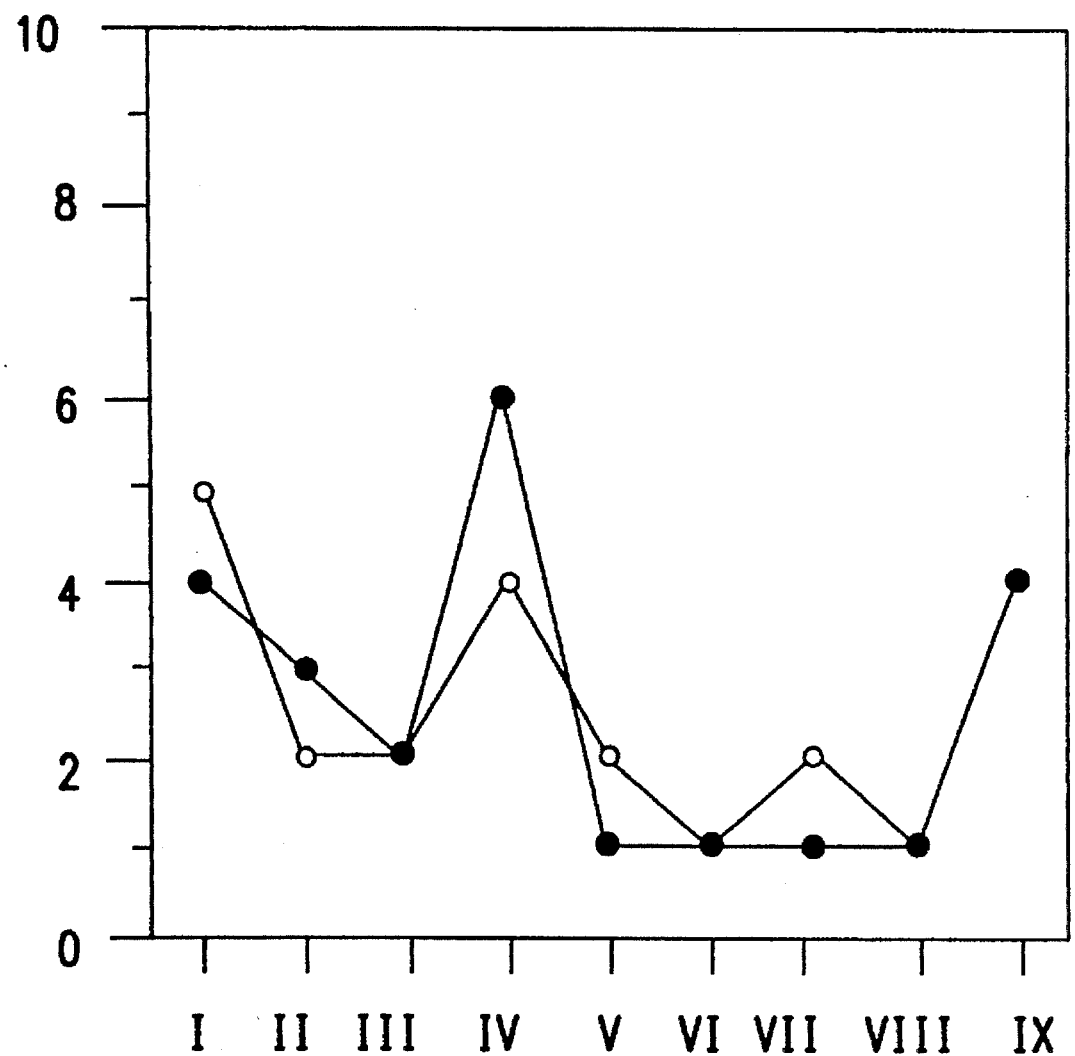

In FIG. 1 the results of such test are reported: said tests were carried out in double blind on 30 patients treated with the calcium salt of MTHF (50 mg/day per os) and on 30 further patients treated with the calcium salt of FTHF (50 mg/day per os) for two weeks, indicating the average score obtained before and after the therapy. In the ascissae of the graph in FIG. 1 are reported the groups of symptoms of the Wittenborn psychiatric scale as defined before, and in the ordinates the average score ±Standard error.

The light coloured column gives the values before the treatment while the dark column gives the values after the treatment. It is evident that the differences found in the medium values cannot be considered significant with MTHF nor with FTHF.

We have also carried out a study in double blind vs. placebo on 10 normofolatemic patients (plasmatic folates comprised between 3 and 17 ng/ml) affected by various psychiatric pathology: the demographic and clinical characteristics of the 10 patients are illustrated in Table II.

This study was carried out by using MTHF (50 mg/day per os in a single administration for two weeks) in the release controlled form (average release time 1 hour).

TABLE II

Demographic and clinical characteristics of 10 normofolatemic patients treated with controlled release Ca salt of MTHF acid in a sole dose of 50 mg/day or with a placebo, for two weeks.

| PATIENT NUMBER | SEX | AGE | DIAGNOSIS (DSM III R)++ | TREATMENT |
| --- | --- | --- | --- | --- |
| 1 | M | 37 | Generalized Anxiety Disorder (300.02) | MTHF Retard |
| 2 | M | 52 | Hysterical neurose with psychomotor agitation (300.11) | Placebo |
| 3+ | F | 62 | Delirium | Placebo |
| 4 | M | 42 | Bipolar disorder (296.52) | MTHF Retard |
| 5 | M | 35 | Generalized Anxiety Disorders (300.02) | Placebo |
| 6 | M | 68 | Senile Dementia | MTHF Retard |
| 7+ | M | 38 | Bipolar Disorders Maniac (296.72) | Placebo |
| 8 | M | 40 | Bipolar Disorder (296.52) | Placebo |
| 9 | F | 52 | Simple phobia (300.29) | MTHF Retard |
| 10 | M | 45 | Generalized Anxiety Disorder (300.02) | MTHF Retard |

+ Dropped after 1 week for exacerbation of symptoms
++ DSM III R = Diagnostic and Statistic Manual III Ed. APA Washington D.C., 1987. The figure in pharenteses indicates the code number assigned to the diagnosis by DSM III R.

The results concerning the treatment of the 5 normofolatemic patients of TABLE II with controlled release MTHF in a sole dose (50 mg/day) per os for two weeks, are represented in FIG. 2 while the results concerning the five patients treated with placebo are represented in FIG. 3, always with reference to the 10 normofolatemic patients described in table II.

In the ascissae of the graphs relating to the 10 patients are reported the 9 groups of symptoms according to the Wittenborn scale, while in the ordinates the seriousness of the symptoms is reported in a scale from 0 to 10; for each group of symptoms the seriousness before (○) and after (●) the treatment is reported.

Figure 4A:
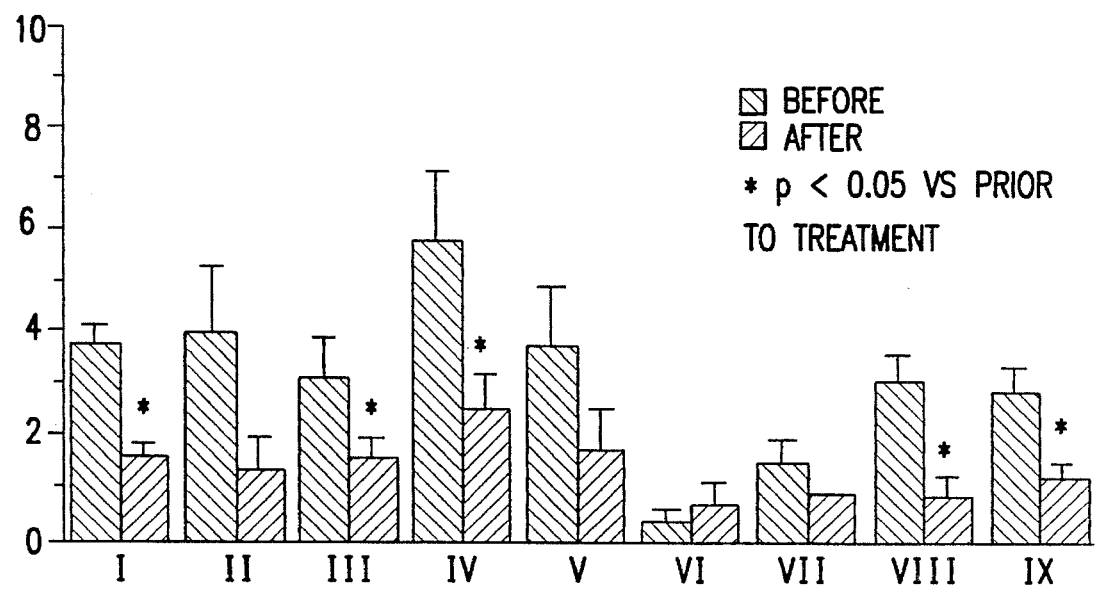
FIG. 4A shows the total average of the seriousness of symptoms determined before and after treatment of five patients with controlled release MTHF.

FIG. 4 comprises the results relative to the study carried out in double blind on 10 patients affected by various psychiatric pathology. In FIG. 4a) is represented the total average of the seriousness of symptoms (±Average Standard Error) determined before and after treatment of the 5 patients with 50 mg/day in a sole dose of controlled release MTHF for two weeks; in the ascissae are also reported the 9 groups of symptoms according to the Wittenborn scale and in the ordinates the seriousness of the symptoms expressed in a scale from 0 to 10.

Figure 4B:
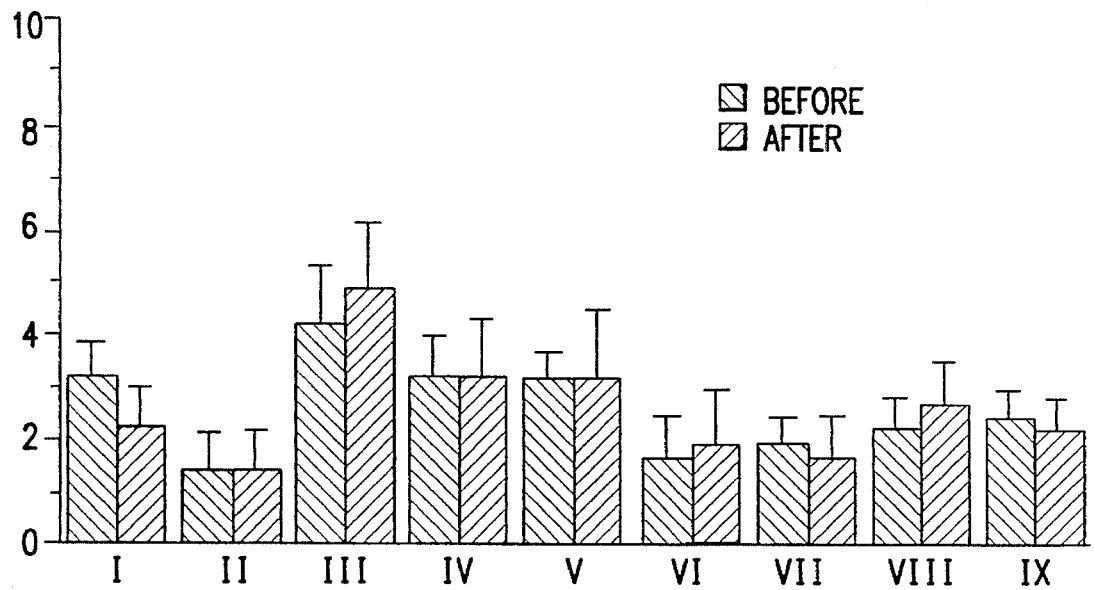
FIG. 4B shows the total average of the seriousness of symptoms measured before and after treatment of five patients given a placebo.

In FIG. 4b) is represented the total average of the seriousness of symptoms (±Average Standard Error) measured before and after treatment of the 5 patients with placebo for two weeks; in the ascissae are also reported the 9 groups of symptoms according to the Wittenborn scale and in the ordinates the seriousness of symptoms expressed on a scale from 0 to 10.

From an examination of the results summarized in FIGS. 1 and 4 it is evident that, administering MTHF or FTHF in non-controlled release form, no practical modification of the Wittenborn scale parameters is observed comparing the values before and after the therapy (FIG. 1), while administering MTHF or FTHF in controlled release form there is a considerable decrease in the score of some parameters of the Wittenborn scale. The pharmacological activity manifested by MTHF in controlled release form is evident when compared to the practically zero activity of the placebo. Such activity is particularly relevant in connection with specific items of the Wittenborn scale illustrated in detail in table III.

TABLE III

List of items of the Wittenborn psychiatric rating scale and of the related improved diagnostic groups in all patients treated with 50 mg/day of controlled release MTHF per os for two weeks.

| NO. OF ITEM | GROUPS | SYMPTOM |
| --- | --- | --- |
| 7 | III, IV | Restlessness |
| 12 | III | Irritability |
| 21 | V, VIII | Disturbance in self-initiated, goal-directed activities |
| 22 | I | Hopelessness |
| 28 | I, IX | Anxiety |
| 35 | III, V, VIII | Aggressiveness |
| 37 | III, V | Mood shifts |
| 41 | IV, V | Indecisiveness |
| 47 | I | Anxiety when facing new circumstances |
| 52 | V, VIII | Impaired capacity to cooperate with others |

We have also carried out a further study with the aim of comparing the effect of the administration of controlled release MTHF (50 mg/day per os) with that of controlled release FTHF at the same dosage. A further group of 40 normofolatemic patients affected by various psychiatric pathology was then selected.

Figure 5A:
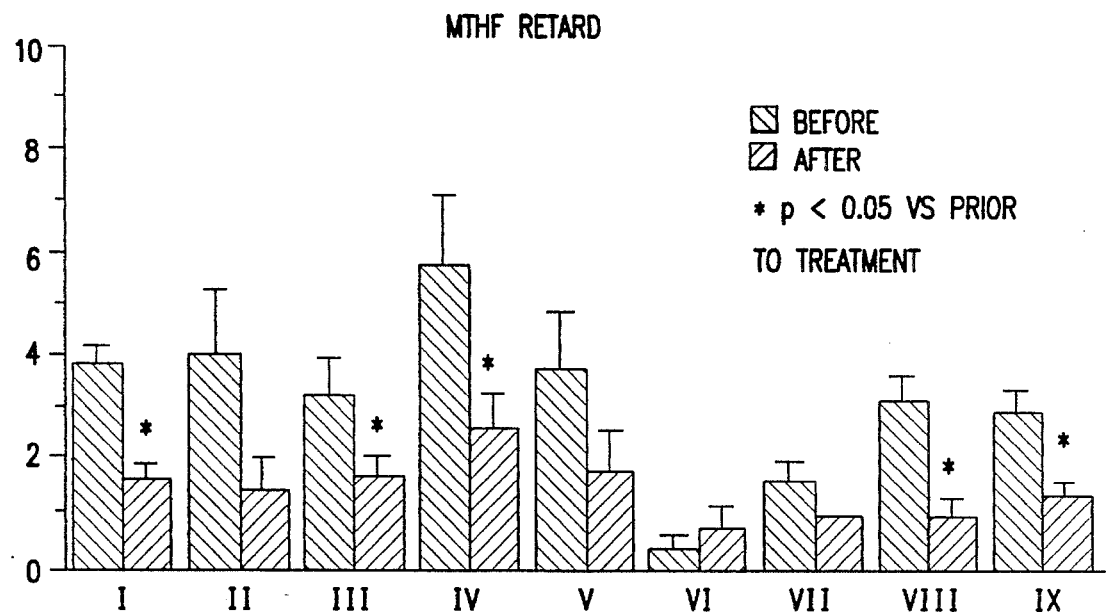
FIGS. 5A and 5B show that patients treated with controlled release MTHF and FTHF have shown a significant decrease of the scores relating to groups I, III, IV, VIII and IX.
Figure 5B:
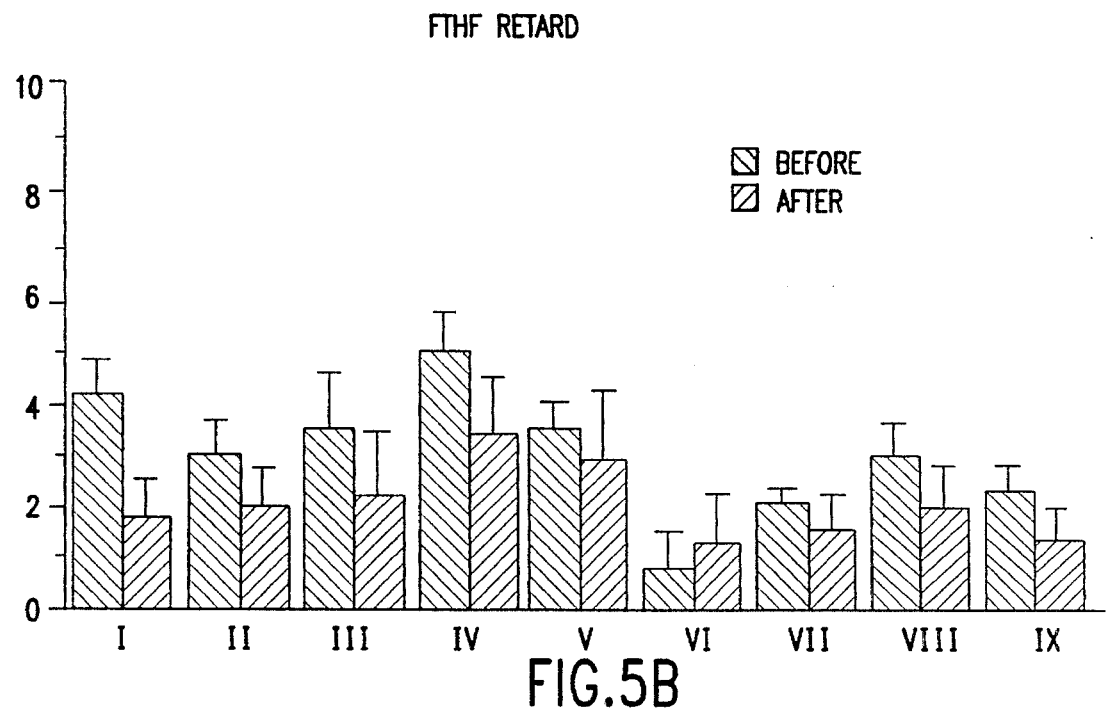
Figure 6:
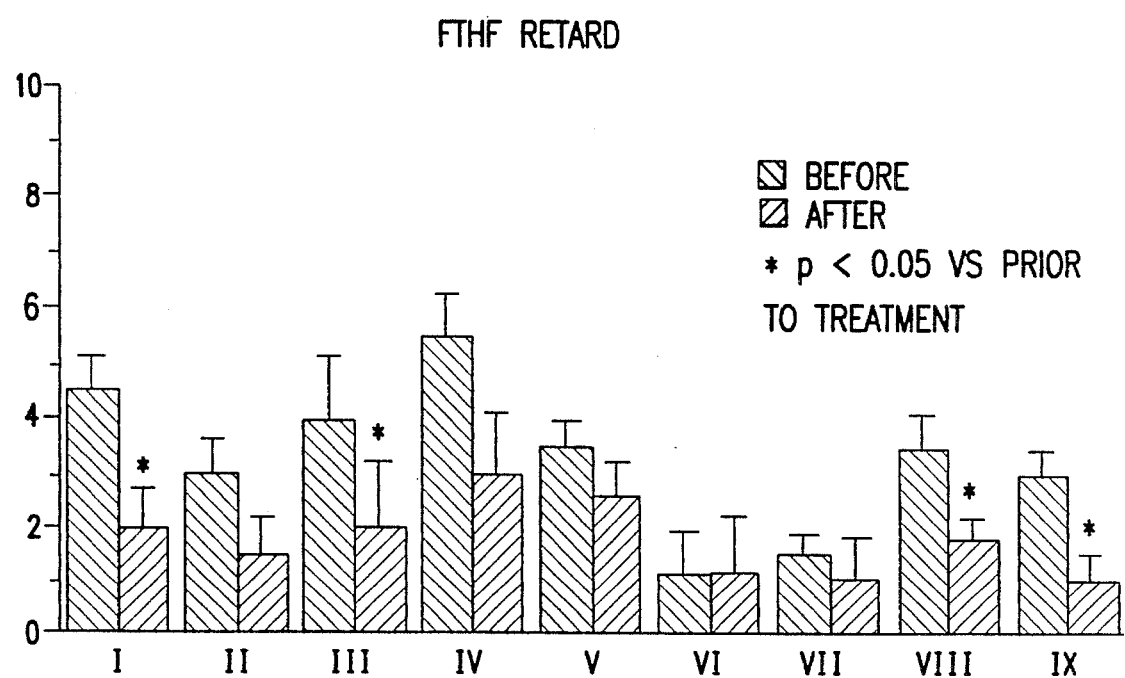
FIG. 6 shows the results of patients treated with controlled release FTHF.

The patients were casually selected for treatment by controlled release MTHF (average release time 1 hour) or by controlled release FTHF (average release time 1 hour) thus obtaining two groups of 20 subjects each, treated For two weeks. The patients treated with 50 mg/day in a sole administration of controlled release MHTF per os have shown a significant decrease of the scopes relating to groups I, III, IV, VIII and IX (FIG. 5a). The patients treated with controlled release FTHF (50 mg/day in a sole administration) have also shown a decrease of the scopes relating to the groups of symptoms I, III, IV, VIII and IX (FIG. 5b) even if such decrease was lower than the one obtained with controlled release MTHF. The use of controlled release FTHF in a higher dosage, 100 mg/day per os in a sole dose, in a similar group of 50 normofolatemic patients treated for 2 weeks, has allowed the reduction in a significant way of the scores of groups I, III, VIII and IX, but proved to be inefficient in improving the symptoms of group IV (FIG. 6).

To provide further evidence for the activity of the pharmaceutical compositions which are an object of the present invention, we report a series of studies carried out in double blind against MTHF in non controlled release form.

The first of such studies was carried out on a group of 24 normofolatemic patients, For whom diagnosis of from light to serious Major Depression was made according to the diagnostic criteria of DMS III R (code 296.2X and 296.3X). The study was carried out in double blind against non controlled release MTHF (50 mg/day per os) with a treatment period of three weeks.

The casual selection of the patients for the treatment resulted in the formation of two homogeneous groups of 12 patients each; one treated with controlled release MTHF (average release time 1 hour) and the, other treated with non controlled release MTHF (both at the dosis of 50 mg/day per os in a sole administration).

The evaluation of the efficacy of the therapy was carried out according to the Hamilton scale for the depression at 31 items.

Figure 7:
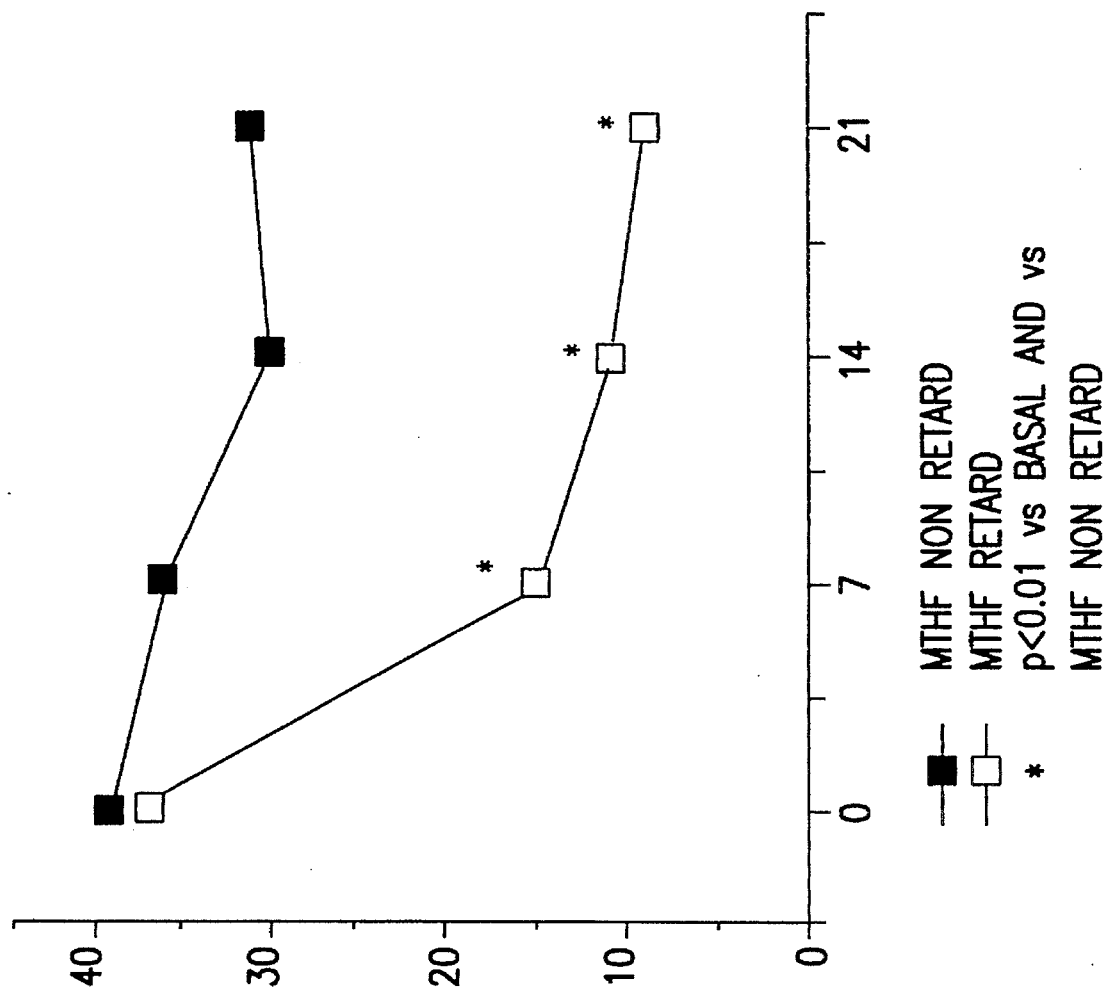
FIGS. 7–9 show a comparison of the results of patients treated with MTHF in controlled release form and non-controlled release form.

The patients were submitted to evaluation before the beginning of the therapy (basal) and after 7, 14 and 21 days of treatment. As can be seen from FIG. 7 (in the ordinates the average score of the Hamilton scale for the 12 patients of the 2 groups and in the ascissae the evaluation times in days during the 3 weeks of treatment are reported) the average score of the Hamilton scale was reduced from 37 at the beginning of the treatment to a value of 10 after three weeks for the group of patients treated with controlled release MTHF, while in the group treated with non controlled release MTHF the decrease of the score was not significant. The decrease of the score of the Hamilton scale appeared significant with respect to the basic value starting from a week after the beginning of the therapy with controlled release MTHF.

Analyzing the single items of the Hamilton scale one can isolate a so called "depressive nucleus" constituted by the items: depression, guilt, suicide, insomnia, loss of interest, psychiatric anxiety and inactivity. The treatment with controlled release MTHF has shown that it is possible to improve said parameters in a significant way.

The second study was carried out on a group of normofolatemic patients responding to the criteria of DMS III R for the diagnosis of disthyemic disturbance (300.40) and of non otherwise specified depression (311.00). The enrolled patients were submitted to a period of wash-out with placebo (that is interruption of the treatment being carried out for the pathology in act and administration of placebo in single blind) of one week. The subjects were evaluated at the beginning and at the end of said period by means of the Hamilton scale fop the depression at 31 items and the Hamilton scale for the anxiety at 14 items; those subjects who at the end of the wash-out period with placebo showed a reduction in the score of the Hamilton scale, higher than 20% with respect to the basic evaluation were excluded from the study.

In this way we have selected 60 subjects not sensitive to the treatment with placebo which were assigned in a casual way to the therapy with controlled release MTHF (50 mg/day, average release time 1 hour, in a sole administration) or with non controlled release MTHF (50 mg/day per os in a sole administration) for three weeks. The randomization has allowed obtaining two homogenous groups of 30 patients each.

Figure 8:
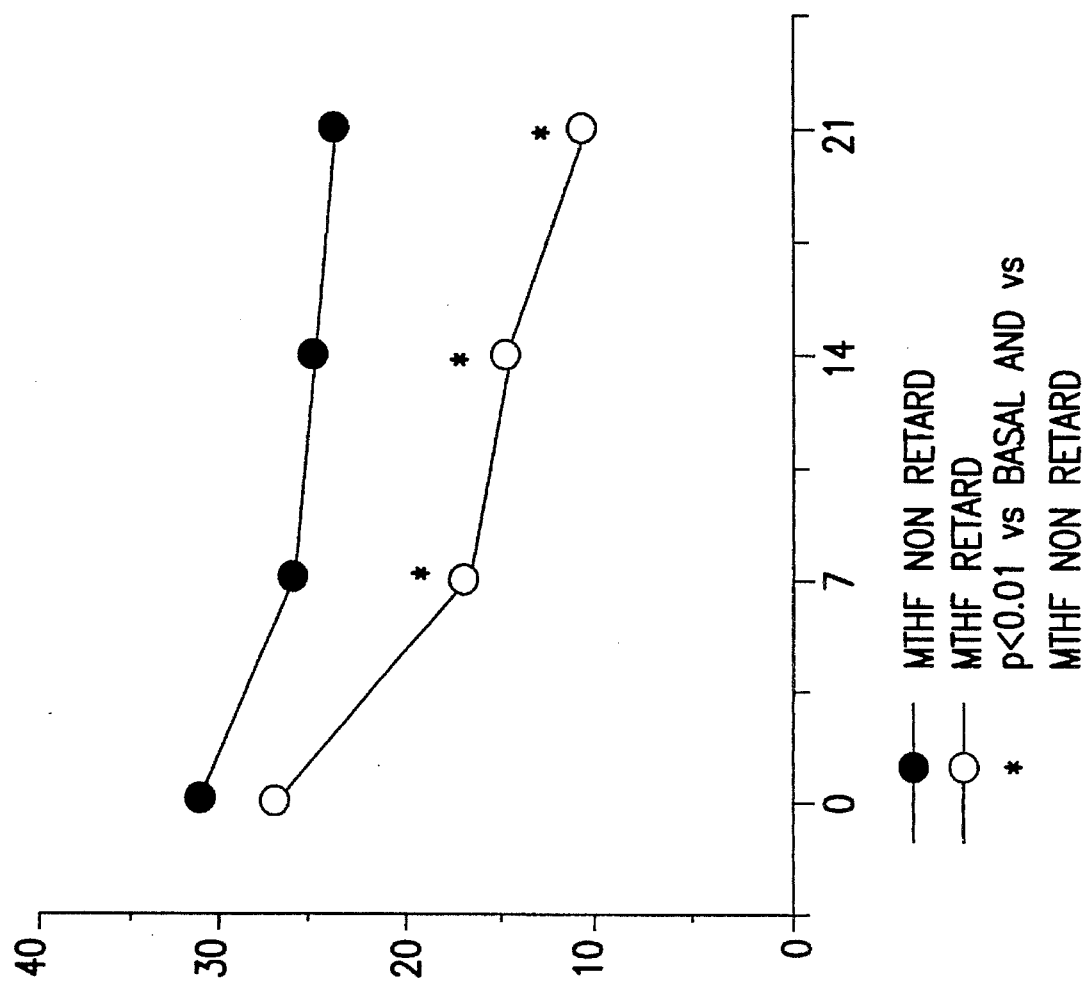

FIG. 8 shows the results of such a study as far as the depressive component is concerned: in the ordinates ape reported the average values of the global score of the Hamilton scale for the depression in the two studied groups; in the ascissae are reported the evaluation times in days during the treatment period of 3 weeks. The patients treated with controlled release MTHF passed from a basic score of 27 in the Hamilton scale fop the depression, to a score of 12 after 3 weeks of therapy. The decrease of such score with respect to the basic value was already significant after one week from the beginning of the treatment. The patients treated with non controlled release MTHF have on the other hand shown a negligeable decrease of the score of the Hamilton scale for the depression. Also in this case one could find evidence, examining the single items of the Hamilton scale, for a significant improvement of the parameters constituting the depressive nucleus in the patients treated with controlled release MTHF. In fact, guilt, suicide, insomnia, loss of interest, psychiatric anxiety, sense of uselessness and indignity were improved in the group treated with controlled release MTHF, while they remained almost unchanged in the group treated with non controlled release MTHF.

Figure 9:
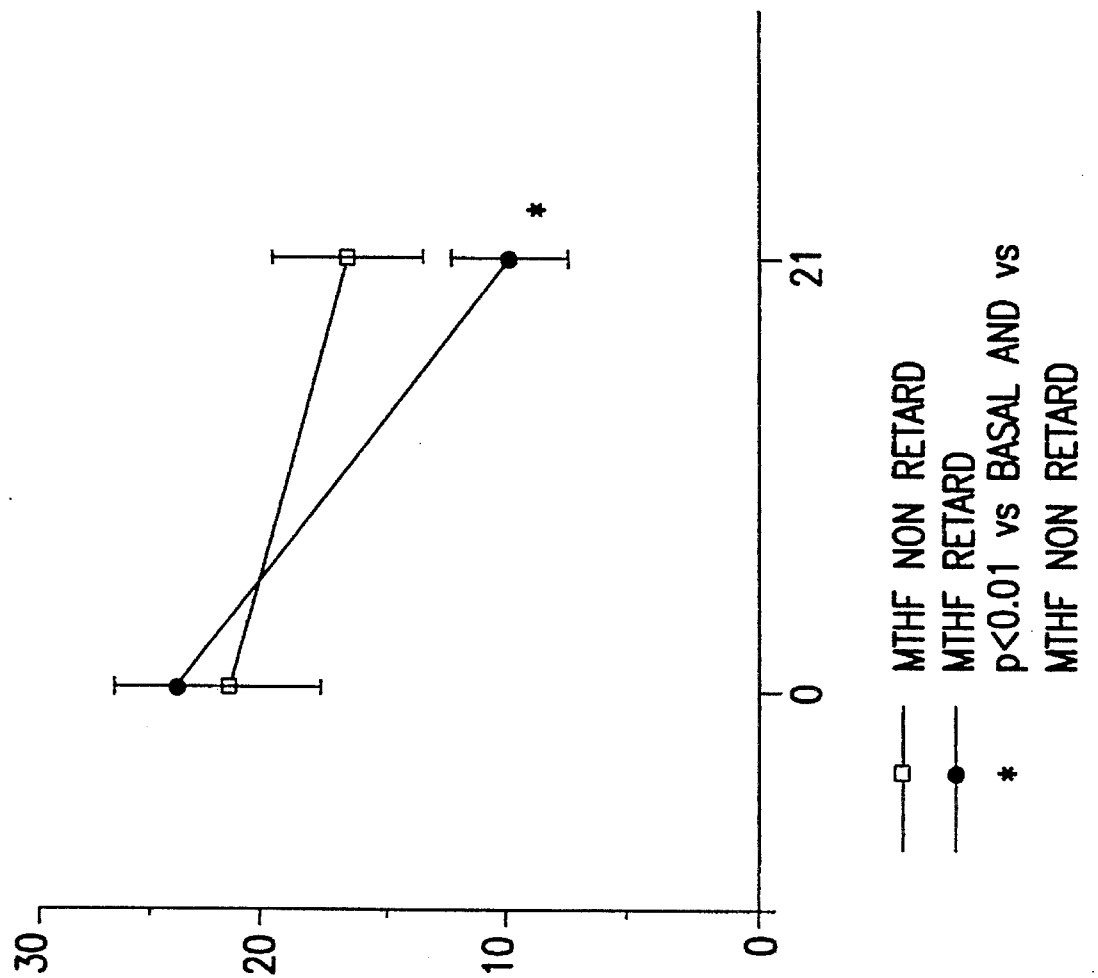

FIG. 9 shows the result of the treatment with controlled release MTHF and with non controlled release MTHF on the global scope (±Standard Error) of the Hamilton scale for the anxiety (in the ordinates) evaluated before and after the therapy (in the ascissae) in the same 2 groups of patients. In the subjects which were treated with controlled release MTHF the average score (±Standard Error) was reduced from 23±5 before the treatment to 11±4 after 21 days of therapy, reaching statistical significance. On the contrary the patients treated with non controlled release MTHF have shown a decrease of the global score of very modest entity.

Analyzing the single items of the Hamilton scale for the anxiety, one could find evidence for an effect of the controlled release MTHF prevalent on the following symptoms: tension (feeling of tension, fatigue, startless, tendency to weep, tremors, restlessness, inability to relax), insomnia (difficulty in going to sleep, nightmares, nocturnal terrors, restless sleep and feeling of fatigue on awakening); intellective sphere (difficulty in concentrating, loss of memory); somatic symptoms: muscular system (muscolar aches, myotasis, stiffness, clonic contractions, clenched teeth, tremulous voice, increase in muscular tone); behaviour of the subject during examination (agitated, restless, goes up and down, tremor of the hands, wrinkled brow, drawn face, sighs or tachypnea, face pallor, deglutition).

Finally, we evaluated the efficacy of controlled release MTHF (50 mg/day per os, in a sole administration, average release time 1 hour) in hypofolatemic patients (plasmatic folates <15 ng/ml and erythrocyte folates <175 ng/ml) affected by depressive disorders. We have verified that such a treatment allows obtaining a significant reduction of the Hamilton scale score for the depression in a shorter time (1 week) with respect to the same dosage of MTHF in non-controlled release form (4 weeks). Therefore the treatment with controlled release MTHF is indicated also in depressive disturbances associated with hypofolatemia.

Similar experiments were carried out using pharmaceutical compositions according to the present invention containing differentiated dosages of controlled release MTHF and controlled release FTHF: 5 mg (20 patients), 10 mg (20 patients), 15 mg (20 patients), 20 mg (20 patients), 25 mg (20 patients), 40 mg (20 patients), 100 mg (20 patients), 200 mg (20 patients) and we have also observed that these dosages produce positive effects on the Wittenborn scale parameters.

Acting differently from all the other drugs employed up to now in the therapy of disthymic conditions, of major depression and of depressive disturbance in general, the pharmaceutical compositions according to the present invention do not interfere with the sleep/wake rythm, do not give sedation, do not confer dependency or addiction and, in general, do not present side effects which is, contrary to all the drugs up to now used for the therapy of depressive disturbances.

Purely for descriptive and non limitative ends, we report now some examples of pharmaceutical compositions according to the present invention.

EXAMPLE 1

Gastroresistant Controlled Release Tablet Containing 10 mg MTHF

Release time=15 or 20 minutes. 1 tablet contains:

| | |
|---|---|
| MTHF calcium salt pentahydrate (equal to MTHF mg 10) | mg 12.6 |
| Pregelatinized starch | mg 115.0 |
| Lactose 100 mesh | mg 72.7 |
| Idroxyipropylmethylcellulose | mg 5.0 |
| Magnesium stearate | mg 1.0 |
| Cellulose acetophtalate | mg 7.5 |
| Diethylphtalate | mg 2.5 |

EXAMPLE 2

Gastroresistant Controlled Release Tablet Containing 15 mg MTHF

Release time=20 or 30 minutes. 1 tablet contains:

| | |
|---|---|
| MTHF calcium salt pentahydrate (equal to MTHF mg 15) | mg 18.8 |
| Pregelatinized starch | mg 115.0 |
| Lactose 100 mesh | mg 60.2 |
| Hydroxyipropylmethylcellulose | mg 5.0 |
| Magnesium stearate | mg 1.0 |
| Cellulose acetophtalate | mg 7.5 |
| Diethylphtalate | mg 2.5 |

EXAMPLE 3

Gastroresistant Controlled Release Tablet Containing 20 mg MTHF

Release time=30 or 35 minutes. 1 tablet contains:

| | |
|---|---|
| MTHF calcium salt pentahydrate (equal to MTHF mg 20) | mg 25.1 |
| Microcrystalline cellulose | mg 80.0 |
| Lactose 100 mesh | mg 79.9 |
| Hydroxyropylmethylcellulose | mg 10.0 |
| Glyceryl beenate | mg 5.0 |
| Cellulose acetophtalate | mg 7.5 |
| Diethylphtalate | mg 2.5 |

EXAMPLE 4

Gastroresistant Controlled Release Tablet Containing 25 mg MTHF

Release time=35 or 40 minutes. 1 tablet contains:

| | |
|---|---|
| MTHF calcium salt pentahydrate (equal to MTHF mg 25) | mg 31.6 |
| Microcrystalline cellulose | mg 80.0 |
| Lactose 100 mesh | mg 73.4 |
| Hydroxypropylmethylcellulose | mg 10.0 |
| Glyceryl beenate | mg 5.0 |
| Cellulose acetophtalate | mg 7.5 |
| Diethylphtalate | mg 2.5 |

EXAMPLE 5

Gastroresistant Controlled Release Tablet Containing 40 mg MTHF

Release time=50 or 60 minutes. 1 tablet contains:

| | |
|---|---|
| MTHF calcium salt pentahydrate (equal to MHTF mg 40) | mg 50.6 |
| Microcrystalline cellulose | mg 80.0 |
| Lactose 100 mesh | mg 54.4 |
| Hydroxypropylmethylcellulose | mg 10.0 |
| Glyceryl beenate | mg 5.0 |
| Cellulose acetophtalate | mg 7.5 |
| Diethylphtalate | mg 2.5 |

EXAMPLE 6

Gastroresistant Controlled Release Tablet Containing 50 mg MTHF

Release time=60 minutes. 1 tablet contains:

| | |
|---|---|
| MTHF calcium salt pentahydrate (equal to MTHF mg 50) | mg 63.2 |
| Microcrystalline cellulose | mg 80.0 |
| Lactose 100 mesh | mg 41.7 |
| Hydroxypropylmethylcellulose | mg 10.0 |
| Glyceryl beenate | mg 5.0 |
| Cellulose acetophtalate | mg 7.5 |
| Diethylphtalate | mg 2.5 |

EXAMPLE 7

Gastroresistant Controlled Release Tablet Containing 50 mg FTHF

Release time=60 minutes. 1 tablet contains:

| | |
|---|---|
| FTHF calcium salt pentahydrate (equal to FTHF mg 50) | mg 66.7 |
| Carboxyvinylpolymer | mg 20.0 |
| Microcrystalline cellulose | mg 112.3 |
| Magnesium stearate | mg 1.0 |
| Cellulose acetophtalate | mg 7.5 |
| Diethylphtalate | mg 2.5 |

EXAMPLE 8

Gastroresistant Controlled Release Tablet Containing 100 mg of MTHF

Release time=90 or 120 minutes. 1 tablet contains:

| | |
|---|---|
| MTHF calcium salt pentahydrate (equal to MTHF mg 100) | mg 126.5 |
| Dibasic calcium phosphate | mg 90.0 |
| Lactose 100 mesh | mg 163.0 |
| Idroxypropylmethylcellulose | mg 15.0 |
| Magnesium stearate | mg 5.5 |
| Cellulose acetophtalate | mg 15.0 |
| Diethylphtalate | mg 5.0 |

EXAMPLE 9

Gastroresistant Controlled Release Tablet Containing 200 mg MTHF

Release time=180 or 210 or 240 minutes. 1 tablet contains:

| | |
|---|---|
| MTHF calcium salt pentahydrate (equal to MTHF mg 200) | mg 251.0 |
| Hydroxypropylmethylcellulose | mg 30.0 |
| Lactose 100 mesh | mg 149.0 |
| Glyceryl beenate | mg 20.0 |
| Cellulose acetophtalate | mg 15.0 |
| Diethylphtalate | mg 5.0 |

EXAMPLE 10

Gastroresistant Controlled Release Tablet Containing 200 mg FTHF

Release time=4 hours. 1 tablet contains:

| | |
|---|---|
| FTHF calcium salt pentahydrate (equal to FTHF mg 200) | mg 266.7 |
| Microcrystalline cellulose | mg 63.3 |
| Castor oil hydrogenated | mg 100.0 |
| Glyceryl beenate | mg 20.0 |
| Cellulose acetophtalate | mg 15.0 |
| Diethylphtalate | mg 5.0 |

EXAMPLE 11

Controlled Release Suppository Containing 50 mg MTHF 1 suppository contains:

| | |
|---|---|
| MTHF calcium salt pentahydrate (equal to MTHF mg 50) | mg 63.2 |
| Hydroxypropylmethylcellulose | mg 50.0 |
| Semisynthetic glycerides | mg 1886.8 |

EXAMPLE 12

Controlled Release Injectable Form Containing 50 mg MTHF 1 vial contains:

| | |
|---|---|
| MTHF calcium salt pentahydrate (equal to MTHF mg 50) | mg 63.2 |
| Glutathion | mg 10.0 |
| Citric Acid | mg 30.0 |
| Hydroxyethylcellulose | mg 10.0 |
| Mannitol | mg 160.0 |
| Methyl p-hydroxybezoate | mg 1.0 |
| Sodium hydroxide | mg 17.7 |

Water for injectable preparations sufficient to ml 3

EXAMPLE 13

Controlled Release Transdermic System Containing 20 mg MTHF 1 transdermic system contains:

| | |
|---|---|
| MTHF calcium salt pentahydrate (equal to MTHF mg 20) | mg 25.1 |
| Fluid silicone | mg 174.8 |
| Precipitated silica | mg 15.2 |

EXAMPLE 14

Controlled Release Transdermic System Containing 50 mg MTHF 1 transdermic system contains:

| | |
|---|---|
| MTHF calcium salt pentahydrate (equal to MTHF mg 50) | mg 63.3 |
| Glycerine | mg 135.0 |
| Polivinyl alcohol | mg 7.5 |
| Polivivylpyrrolidone | mg 5.0 |
| Citric acid | mg 2.5 |
| Purified water | mg 100.0 |

The present invention is susceptible of numerous modifications and variations, all of which are comprised in the inventive concept. Furthermore all the details can be substituted by technically equivalent ones.

I claim:

1. A therapeutic method for treating major depression, dysthymia and non-otherwise specified depressive disturbances in normofolatemic individuals, consisting essentially of administering to an individual having a serum folate level of between 3 and 17 ng/ml, a therapeutically effective amount of 5-methyltetrahydrofolic acid (MTHF) or 5-formyltetrahydrofolic acid (FTHF), or a pharmaceutically acceptable salt thereof as the sole therapeutically active agent, in a controlled release form wherein said MTHF or FTHF is released over a time period of between 15 minutes and 8 hours.

2. A therapeutic method according to claim 1, wherein MTHF, FTHF, or their pharmaceutically acceptable salts are administered in the form of a controlled release pharmaceutical composition having a release time ranging from 20 to 60 minutes.

3. A therapeutic method according to claim 1, wherein MTHF, FTHF, or their pharmaceutically acceptable salts are administered in the form of a controlled release pharmaceutical composition containing them in amounts ranging from 5 to 200 mg.

4. A therapeutic method according to claim 1, wherein MTHF, FTHF, or their pharmaceutically acceptable salts are administered in the form of a controlled release pharmaceutical composition containing them in amounts ranging from 10 to 50 mg.

5. A therapeutic method according to claim 1, wherein MTHF, FTHF, or their pharmaceutically acceptable salts are administered by oral route in the form of a controlled release gastrosoluble or enterosoluble composition.

6. A therapeutic method according to claim 1, wherein MTHF, FTHF, or their pharmaceutically acceptable salts are administered in the form of a controlled release injectable composition.

7. A therapeutic method according to claim 1, wherein MTHF, FTHF, or their pharmaceutically acceptable salts are administered by rectal route in the form of controlled release suppositories.

8. A therapeutic method according to claim 1, wherein MTHF, FTHF, or their pharmaceutically acceptable salts are administered by transdermal route in the form of a controlled release transdermal composition.

* * * * *